United States Patent [19]
Carosino et al.

[11] Patent Number: 5,310,433
[45] Date of Patent: May 10, 1994

[54] PROCESS FOR PREPARING HIGH ENERGY ROCKET PROPELLANT PLASTICIZER FROM GLYCEROL

[75] Inventors: Lawrence E. Carosino, Wilmington, Del.; Kenneth O. Hartman, LaVale, Md.

[73] Assignee: Hercules Incorporated, Wilmington, Del.

[21] Appl. No.: 137,842

[22] Filed: Dec. 24, 1987

[51] Int. Cl.⁵ .................. C06B 25/14; C06B 45/10
[52] U.S. Cl. .................. 149/104; 149/19.1; 149/88; 558/484; 558/486
[58] Field of Search .......... 149/88; 558/480, 484, 558/486, 487; 568/680

[56] References Cited

U.S. PATENT DOCUMENTS

| | | | |
|---|---|---|---|
| H488 | 3/1988 | Farncomb et al. | 558/484 |
| 1,936,020 | 11/1933 | Hough | 558/484 |
| 2,139,364 | 12/1938 | Groll | 149/102 |
| 3,002,830 | 10/1961 | Barr | 149/19.4 |
| 3,009,944 | 11/1961 | Brunnberg | 558/486 |
| 3,856,691 | 12/1974 | Haugen et al. | 568/680 X |
| 3,931,338 | 1/1976 | Rupilius | 568/680 |
| 3,956,890 | 5/1976 | Davis | 60/219 |
| 4,000,179 | 12/1976 | Ayerst | 558/486 |
| 4,352,699 | 10/1982 | Zeigler, Jr. | 149/109.6 |
| 4,360,698 | 11/1982 | Sedon | 568/680 X |
| 4,687,755 | 8/1987 | Green | 568/680 X |

*Primary Examiner*—Robert L. Stoll
*Assistant Examiner*—John M. Covert
*Attorney, Agent, or Firm*—John E. Crowe

[57] ABSTRACT

An efficient method for preparing nitrated glycerol glycol ether useful as a high energy plasticizer, by using as nitrator feed, the reaction products of an alkali metal bisulfate-catalyzed reaction of ethylene oxide and a stoichiometric excess of glycerol.

8 Claims, No Drawings

PROCESS FOR PREPARING HIGH ENERGY ROCKET PROPELLANT PLASTICIZER FROM GLYCEROL

This invention is concerned with an efficient method for producing stable high energy plasticizer composition for cross-linked double based rocket propellant material from glycerol and ethylene oxide by use of an initial catalyzed reaction to obtain intermediate reaction products suitable as direct conitrator feed.

BACKGROUND

Use of high energy nitrate derivatives of various polyhydroxy alcohols are known in the high explosives and propellant arts, particularly as energetic organic plasticizers for cross-linked double based rocket propellant compositions.

Because of the vulnerability of rocket propellant materials to low temperature extremes, particularly the tendency of double based solid propellants to become embrittled and to crack, causing irregular burning properties, it is found useful to incorporate mixed energetic organic plasticizers to prevent crystallization. By way of example, mixtures of 1, 2, 4-butanetriol trinitrate (BTTN), triethylene glycol dinitrate (TEGDN), nitroglycerine (NG), as well as glycerol glycol ether (GGE) can be used in nitrated form as glycerol glycol ether trinitrate (ROC), for such purpose.

Of the above compounds, however, the nitrate derivative of glycerol glycol ether, glycerol glycol ether trinitrate (ROC) in combination with nitroglycerine (NG), is found particularly suitable because of its high energy content and low volatility. Such composition, however, is expensive and time consuming to safely produce by traditional conitration reaction. This is so because of the need to separate out or purify the primary GGE intermediate product to eliminate sodium chloride and minimize ethylene glycol content which, respectively, cause corrosion and production of a volatile dinitrate in the nitrator.

A frequently used art process for obtaining GGE (i.e. Kharasch synthesis) is generally represented by the following reaction:

I. HOCH$_2$CH$_2$OH +

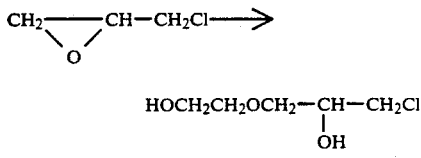

$$\xrightarrow[H_2O]{Na_2CO_3}$$

-continued
HOCH$_2$CH$_2$OCH$_2$CHCH$_2$—OH (GGE).
|
OH

A number of by-products are obtained by this process, and the required distillation steps to obtain GGE are further complicated by precipitation of dissolved salts from the hydrolysis step.

It is an object of the present invention to produce high energy plasticizer composition suitable for cross-linked double based rocket propellant.

It is a further object of the present invention to cheaply and efficiently produce high energy plasticizer composition comprising glycerol glycol ether trinitrate and nitroglycerine in controlled ratios and with predictable stability using glycerol and ethylene oxide as raw material.

THE INVENTION

The above objects can be realized by utilization of a catalyzed two-step process for producing high energy plasticizer composition for cross-linked double based rocket propellant comprising
(a) contacting ethylene oxide and glycerol in the presence of a catalytic amount of dry alkali metal bisulfate, particularly the potassium and/or sodium salt;
(b) separating out the alkali metal bisulfate catalyst; and
(c) conitrating the resulting intermediate product mix, without further purification, to obtain the desired high energy plasticizer composition.

The process of the instant invention is conveniently represented by the following reaction:

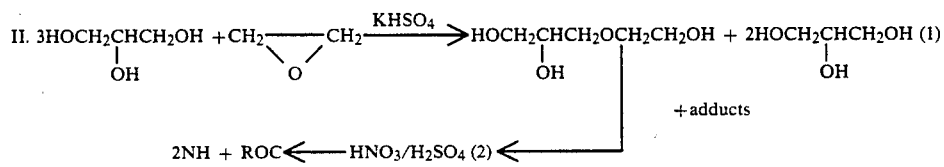

in which "ROC" and "NG" are defined as above indicated, the second step representing an art-recognized conitration step using mixed nitrating acid as hereafter described.

Reaction-wise the amount of glycerol-to-ethylene oxide reactant of the instant-process can usefully vary within a molar ratio of about 1–5 to 1, and preferably falls within a range of about 2–4 to 1, the relative molar concentration of glycerol-to-ethylene oxide being generally determined by (a) the desired ratio of NG-to-ROC in the final (conitrated) product, (b) the need to minimize production of ethylene glycol and control wasteful chaining reactions which can occur in the presence of a nucleophilic agent, and (c) a desire for a good yield of the high energy ROC plasticizer product.

Temperature-wise, step (1) of the instant process is best carried out at about 20° C.–55° C. and preferably at about 30° C.–40° C. at a pressure of about 0–50 psig.

The ethylene glycol and chaining reaction problems, noted above, are well recognized in the art (ref K. Weissermel and H. J. Arpe, Industrielle Organische Chemie, Verlag Chimie GmbH, Weinheim Germany 1976, pp 176–177), and can be further identified with the following reactions:

HOCH$_2$CH$_2$OCH$_2$—CH—CH$_2$Cl
|
OH

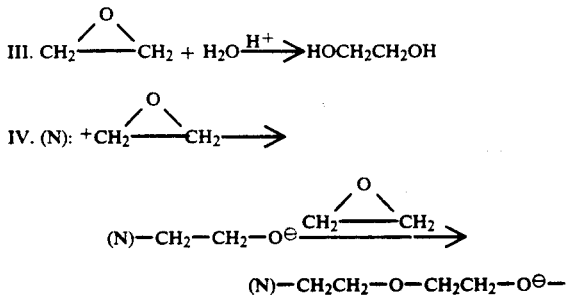

, and so forth, where "(N)" represents a nucleophilic agent such as water or an alcohol in which hydrolysis of ethylene oxide (EO) to form ethylene glycol (formula III) is achieved commercially by an acid catalyzed reaction with water, using a mole ratio of water-to-ethylene oxide of 10:1. Even with so large an excess of water, however, some chaining of EO occurs (formula IV), and nitratable diethylene glycol is produced in substantial amount.

Current attempts to control chaining and avoid production of ethylene glycol dinitrate and similar by-product reactions by use of excess glycerol alone (i.e. in the absence of the instant catalyzed reaction), results in increased production of various intermediate isomeric adducts (ref formulae V, VI, VII and VIII below):

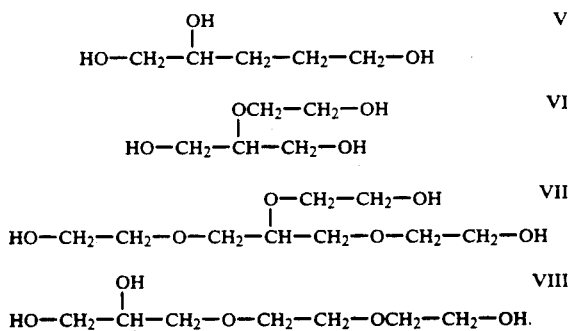

To the degree that such adducts are formed and are ultimately converted into nitrate esters, they represent a loss in energy of the total reaction system.

For purposes of the present invention, however, it is preferred to carry out the first reaction step under essentially anhydrous conditions, and to maintain strict control over the reactants to limit production of ethylene glycol intermediate to about 0.5% by weight or less. In this way one can correspondingly limit production of glycol dinitrate, a volatile compound, in the final product.

Dry alkali bisulfate catalyst used in the instant process includes $KHSO_4$ and/or $NaHSO_4$, preferably in the form of anhydrous powder or as fines, conveniently suspended in glycerol. A catalytic amount, for present purposes, can vary from about 3-15 wt. % or more, and is preferably used in a concentration of about 6-10 wt. %, based on the initial reaction mixture.

Suitable anhydrous bisulfate material is commercially obtainable, for instance, in reagent grade powdered form from Aldrich Chemical Company of Milwaukee, Wis.

The reaction shown in formula II supra is conveniently carried out, for example, by first suspending a desired amount of anhydrous $KHSO_4$ fines in glycerol with rapid stirring to assure free movement of the fines or particles within the reactor. Liquid ethylene oxide reactant is then added in small increments to the reactor to obtain a mole ratio of glycerol-to-ethylene oxide of 1-5 to 1, the rate of addition being carefully controlled to limit the resulting exothermic reaction and maintain the reaction mixture within the above-indicated temperature and pressure range.

Upon completion of the initial reaction step, undissolved catalyst is separated from intermediate products by pressure filtration or vacuum filtration, using a suitable art recognized filtration medium, the catalyst being normally kept in dry condition and recycled.

In accordance with the present process, the conitration reaction step (Step 2) can then be carried out, using all of the intermediate products of Step 1 (with possible minor amounts of dissolved catalyst) without further distillation or purification.

The conitration step is usefully carried out in a conventional batch process by, using cooled nitrating acid comprising about 45 wt %-65 wt % concentrated nitric acid and 35 wt %-55 wt % concentrated sulfuric acid, and up to about 7 wt % water. The resulting intermediate products from Step 1 are then slowly added (in toto) into the vortex of cool stirred nitrating acid in a stainless steel nitrator maintained at a temperature of about 15° C. by use of cooling coils.

For present purposes, it is again found advisable to limit the rate of addition the Step 1 intermediates into the nitrator at a rate sufficient to maintain an optimal ratio of nitrating acid to organic feed to permit the reaction to safely proceed for up to a 60 minute period.

The conitrated products are then allowed to separate out and are recovered by conventional phase separation technique from the spent acid, neutralized, and water washed in the usual manner.

The instant invent ion is further demonstrated but not limited by the following examples and Tables.

EXAMPLE 1

A. The initial catalyzed reaction step to form glycerol glycol ether (GGE) from glycerol and liquid ethylene oxide, is conveniently carried out in a 500 ml heavy walled glass reaction vessel[*1] having a stainless steel head equipped with entry ports fitted with an air driven high torque agitator, a thermocouple temperature probe, a valved gas inlet tube of 8 gauge stainless steel extending to the bottom of the reactor, a pressure-vacuum gauge, a valved sampling and purging tube connected to a nitrogen gas source, and a pressure relief valve set at 50 psig. The described reactor is suitably connected through the gas inlet tube and a valved glass tubing to a shielded graduated glass reservoir[*1] containing liquified ethylene oxide reactant. The reservoir and reactor components are conveniently balance-mounted to permit accurate monitoring of the amount and rate at which ethylene oxide reactant is fed into the reactor.

*1 Fischer-Porter Company, Warminster, Pa.

B A second, or conitration step, is carried out using a 3 liter jacketed stainless steel reaction vessel capable of cooling and holding concentrated nitric/sulfuric acid mix and filtered intermediate product(s) obtained from the initial catalyzed reaction step carried out using the equipment described in Example 1A supra. The reactor used for carrying out the conitration step is conveniently equipped with a feeding port, a rotating mechanical stirring paddle, and a bottom-valved dumping port, a temperature sensing and cooling means, and pressure sensing means of conventional types;

C. The glass reactor described in A supra is charged with 184 grams (2.0 mole) of glycerol, into which is vigorously stirred 34 grams of fine reagent grade anhydrous crystalline potassium bisulfate at room temperature. The reactor is then evacuated by aspirator vacuum and flushed 3 times with nitrogen gas before final evacuation. A weighed amount of liquid ethylene oxide sufficient to obtain a 2:1 mole ratio of glycerol-to-ethylene oxide is then withdrawn from the glass reservoir and added to the reactor in small increments with continuous stirring over a 3 hour period, while maintaining the reaction mixture at a temperature ranging from about 25° C.–28° C. Pressure in the reactor quickly rises 10–15 psig after each addition of ethylene oxide then subsides. When all of the ethylene oxide reactant has been added to the reactor and the pressure stabilizes, the reactor is pressured with nitrogen up to 25 psig and allowed to stand overnight at ambient temperature. A negligible pressure drop is observed over this period.

After venting the nitrogen atmosphere, the resulting intermediate products, comprising GGE, glycerol and various adducts, are suction filtered to remove most of the suspended $KHSO_4$ catalyst, leaving a viscous water-clear product. Samples are then analyzed by the GLC method[*1A] using a gas chromatograph with a flame ionization detector (Applied Science Laboratories, State College, Pa.) and the results recorded in Table I below as S-7.

*1A Sample dissolved in pyridine then reacted with trimethyl chlorosilane (Pierce Chemical Company of Rockford, Ill.) to obtain the trimethylsilyl ether and then volatilized.

EXAMPLE 2

The reaction described in Example 1C is repeated four times, utilizing about 34 grams $KHSO_4$ and glycerol/ethylene oxide reactants having molar ratios of 3 to 1, and 4 to 1 respectively; and the resulting individual intermediate product mixtures are then analyzed and reported in Table 1 below as S-1, S-2, S-3 and S-6.

EXAMPLE 3

The catalyzed reactions described in Example 1C is repeated utilizing 17 gram and 8.5 gram amounts of dry $KHSO_4$ catalyst and a glycerol/ethylene oxide molar ratio of 3 to 1 respectively. The resulting intermediate product mixture are analyzed as before and reported in Table 1 as samples S-4 and S-5.

EXAMPLE 4

A. Mixed intermediate products identified as samples S-8 and S-9 are obtained on a pilot plant scale (25–35 lb) in accordance with the reaction described in Example 1C, using a proportional amount of $KHSO_4$ and a 3 to 1 molar ratio of glycerol/ethylene oxide reagents. The resulting filtered intermediate product is found to contain the following components:

| Composition (% In by wt.) | Sample S-8 | Sample S-9 |
| --- | --- | --- |
| Glycerin | 60.4 | 61.9 |
| GGE | 29.8 | 29.5 |
| Di-adduct | 6.6 | 6.3 |
| Tri-adduct | 1.0 | 0.9 |
| Ethylene glycol | 0.9 | 0.2 |
| Potassium bisulfate | 1.5 | 1.1 |

B. Two six hundred seventy-seven (677) gram samples of S-8 and S-9 reaction mix from Example 4A are separately conitrated, using the nitration equipment and general conditions described in Example 1B at 15° C. for 38 minutes (S-8) and 52 minutes (S-9) respectively. The nitrating acid used in each case is concentrated nitric acid/sulfuric acid mix having a weight ratio of 2.59 to 1 at 18°–20° C. After standing for 30 minutes, the spent acid and raw oil conitration product separate out and are drawn off. Small amounts of each oil product (14 grams) are then removed for stability tests[*5]. Each unwashed nitrated oil product, containing ROC, NG and various nitrated intermediates pass the stability test by remaining stable for 20 at least hours at room temperature without fume off: the corresponding spent acid passed the stability test by remaining stable for over 66 hours at 60° C. without fume off occurring;

*5 The 100 ml Scale Stability Test.

C. The remaining samples of conitrated product(s) from Example 4A are then neutralized with weak sodium carbonate solutions and washed 10 times in distilled water at 25° C. The neutralized products are analyzed and the results reported in Table II below.

TABLE II

| | CHEMICAL ANALYSES | |
| --- | --- | --- |
| Run No. | Sample S-8 | Sample S-9 |
| PRODUCT ANALYSES: | | |
| ROC, % by wt. | 25.0 | 24.9 |
| NG, % | 75.0 | 75.1 |
| Nitrogen, % | 17.1 | 17.1 |
| $H_2$, % | 0.35 | 0.31 |
| Acidity, % | 0.001 | 0.0001 |
| KI, min. | 11 | 12 |

TABLE I

| | | | Catalyzed Step 1 Reaction[*1] | | | | | | | |
| --- | --- | --- | --- | --- | --- | --- | --- | --- | --- | --- |
| Sample | Ethylene Oxide (EO) (grams) | Glycerol/EO Mole Ratios | Catalyst (grams) | Reaction Time (hrs.) | Temp. (°C.) | Product (gram) | Yield[*2] (%) | Glycerol Reacted (wt. %) | Isomeric By-Product Adducts (wt. %)[*4] | | |
| | | | | | | | | | 1° | 2° | 3° |
| S-1 | 29.5 | 3/1 | 34.0 | 3.3 | 24–27 | 211.5 | 99.0 | 65.8 | 28.5 | 4.5 | — |
| S-2 | 30.4 | 3/1 | 34.4[*3] | 5.3 | 24–27 | 221.1 | 100.0 | 65.2 | 27.0 | 4.5 | — |
| S-3 | 29.5 | 3/1 | 34.4 | 2.5 | 24–30 | 210.0 | 98.5 | 72.5 | 23.8 | 3.7 | — |
| S-4 | 29.5 | 3/1 | 17.0 | 3.8 | 24–25 | 207.0 | 97.0 | 61.3 | 30.5 | 7.0 | 1.2 |
| S-5 | 29.5 | 3/1 | 8.5 | 3.8 | 24–25 | 203.0 | 95.0 | 66.4 | 24.5 | 4.5 | 0.6 |
| S-6 | 22.0 | 4/1 | 34.0 | 3.8 | 27–44 | 200.0 | 97.0 | 70.5 | 23.9 | 4.5 | 0.5 |
| S-7 | 44.1 | 2/1 | 34.0 | 4.3 | 27–39 | 216.0 | 95.0 | 51.3 | 31.7 | 11.9 | 3.1 |

[*1] using dry finely divided $KHSO_4$ catalyst suspended in 184.2 grams glycerol.
[*2] based on weight of EO reacted.
[*3] filtered and recycled catalyst (wet weight).
[*4] 1° = mono-ethylene oxide adduct.
2° = di-ethylene oxide adducts.
3° = tri-ethylene oxide adducts.

TABLE II-continued
CHEMICAL ANALYSES

| Run No. | Sample S-8 | Sample S-9 |
| --- | --- | --- |
| Mod. Taliani, mm Hg (w/1% stab.) | | 22 |
| SPENT ACID ANALYSIS: | | |
| $HNO_3$, % | 15.4 | 14.4 |
| $H_2SO_4$, % | 69.9 | 70.6 |
| $HNOSO_4$, % | 0.66 | 0.57 |
| $H_2O$, % | 10.1 | 10.6 |
| Oxidizables, % | 3.90 | 3.85 |
| SOUR WATER ANALYSES: | | |
| $HNO_3$, % | 2.05 | 19.6 |
| $H_2SO_4$, % | 0.30 | 4.01 |
| $HNOSO_4$, % | — | — |
| $H_2O$, % | 95.4 | 74.0 |
| Oxidizables, % | 2.30 | 2.36 |
| SWEET WATER ANALYSES: | | |
| Oxidizables, % | 0.71 | 1.01 |
| pH | 9.5 | 9.4 |

What we claim and desire to protect by Letters Patent is:

1. A process for producing high energy plasticizer composition for rocket propellant comprising
   (a) contacting glycerol and ethylene oxide in the presence of a catalytic amount of dry alkali metal bisulfate;
   (b) separating out the alkali metal bisulfate; and
   (c) conitrating the resulting intermediate reaction products, to obtain the desired high energy plasticizer composition.

2. The process of claim 1, in which the dry alkali metal bisulfate is potassium bisulfate and the plasticizer composition comprises glycerol glycol ether trinitrate (ROC) and nitroglycerine (NG).

3. The process of claim 1, in which the dry alkali metal bisulfate catalyst is sodium bisulfate and the plasticizer composition comprises glycerol glycol ether trinitrate (ROC) and nitroglycerin (NG).

4. The process of claim 1, in which the alkali metal bisulfate catalyst is initially suspended in glycerol and the intermediate reaction products are obtained at a temperature of about 20° C.–55° C.

5. The process of claim 1, in which the intermediate reaction products are obtained by contacting glycerol and ethylene oxide in a mole ratio of about 1–5 to 1.

6. The process of claim 1, in which intermediate reaction products are obtained by contacting glycerol and ethylene oxide in a mole ratio of about 2–4 to 1.

7. The process of claim 6 in which the intermediate reaction products are obtained by contacting glycerol and ethylene oxide at a temperature of about 30° C.–45° C.

8. The process of claim 6, in which the intermediate reaction products are obtained by contacting glycerol and ethylene oxide at a pressure of about 0–50 psig.

* * * * *